United States Patent
Wellings

(10) Patent No.: US 8,906,404 B2
(45) Date of Patent: Dec. 9, 2014

(54) THREE DIMENSIONAL POROUS POLYMERIC STRUCTURE HAVING A PORE-SIZE RANGE OF 1/10 TO 10 TIMES THE AVERAGE PORE SIZE

(75) Inventor: Donald A. Wellings, Runcorn (GB)

(73) Assignee: Spheritech Ltd., Runcorn, Cheshire (GB)

( * ) Notice: Subject to any disclaimer, the term of this patent is extended or adjusted under 35 U.S.C. 154(b) by 0 days.

(21) Appl. No.: 13/496,279

(22) PCT Filed: Sep. 16, 2010

(86) PCT No.: PCT/EP2010/005699
§ 371 (c)(1),
(2), (4) Date: Aug. 16, 2012

(87) PCT Pub. No.: WO2011/032705
PCT Pub. Date: Mar. 24, 2011

(65) Prior Publication Data
US 2012/0309053 A1  Dec. 6, 2012

(30) Foreign Application Priority Data
Sep. 16, 2009  (GB) .................................. 0916281.9

(51) Int. Cl.
| | |
|---|---|
| A61F 2/02 | (2006.01) |
| C08J 9/32 | (2006.01) |
| B01J 13/22 | (2006.01) |
| C08J 9/224 | (2006.01) |
| C12N 11/08 | (2006.01) |
| C12P 7/64 | (2006.01) |
| B01J 20/286 | (2006.01) |
| B01J 20/32 | (2006.01) |
| B01J 20/28 | (2006.01) |

(52) U.S. Cl.
CPC .. *C08J 9/32* (2013.01); *B01J 13/22* (2013.01); *C08J 9/224* (2013.01); *C12N 11/08* (2013.01); *C12P 7/6418* (2013.01); *C12P 7/649* (2013.01); *B01J 20/286* (2013.01); *B01J 20/3268* (2013.01); *B01J 20/28011* (2013.01); *B01J 20/28021* (2013.01); *Y02E 50/13* (2013.01)
USPC ....................................................... 424/425

(58) Field of Classification Search
CPC ..... A61K 9/0024; A61L 27/54; A61L 31/146
See application file for complete search history.

(56) References Cited

U.S. PATENT DOCUMENTS

| | | | |
|---|---|---|---|
| 3,991,020 | A | 11/1976 | Alvares et al. |
| 3,996,654 | A | 12/1976 | Johnson |

(Continued)

FOREIGN PATENT DOCUMENTS

| | | |
|---|---|---|
| CN | 2530451 Y | 1/2003 |
| CN | 101291948 A | 10/2008 |

(Continued)

OTHER PUBLICATIONS

International Search Report for Application No. PCT/EP2010/005699 dated Mar. 28, 2011.

(Continued)

*Primary Examiner* — Carlos Azpuru
(74) *Attorney, Agent, or Firm* — Lathrop & Gage LLP; Brian C. Trinque; Giulio A. DeConti

(57) ABSTRACT

Provided herein is a three dimensional porous structure formed around an array of particles, where the particles define pores in the structure. The structure retreats away from the surface of the particles during formation, such that the particles optionally remain within the pores in the structure.

13 Claims, 8 Drawing Sheets supermacroporous silica

(56) References Cited

U.S. PATENT DOCUMENTS

| | | |
|---|---|---|
| 4,582,756 A | 4/1986 | Niinuma et al. |
| 4,711,863 A | 12/1987 | Streat et al. |
| 4,811,402 A | 3/1989 | Ward |
| 5,079,156 A | 1/1992 | Mauz et al. |
| 5,186,838 A | 2/1993 | Simon et al. |
| 5,211,993 A | 5/1993 | Kolesinski |
| 6,372,472 B1 | 4/2002 | Nehls et al. |
| 6,897,271 B1 * | 5/2005 | Domschke et al. .............. 526/91 |
| 2001/0031796 A1 | 10/2001 | Peretti et al. |
| 2005/0271871 A1 | 12/2005 | Yamazaki et al. |
| 2008/0182052 A1 | 7/2008 | Broadus et al. |

FOREIGN PATENT DOCUMENTS

| | | |
|---|---|---|
| CN | 101326005 A | 12/2008 |
| DE | 4234691 A1 | 4/1993 |
| EP | 0357479 A1 | 7/1990 |
| EP | 1632537 A1 | 8/2006 |
| EP | 1947121 A1 | 7/2008 |
| FR | 2605237 A1 | 4/1988 |
| GB | 802329 A | 10/1958 |
| GB | 1467785 A | 3/1977 |
| GB | 2194246 A | 3/1988 |
| JP | 10182761 A | 7/1998 |
| JP | 2004027195 A | 1/2004 |
| JP | 2004097687 A | 4/2004 |
| JP | 2005179493 A | 7/2005 |
| JP | 2009079086 A | 4/2009 |
| SU | 617427 A1 | 7/1978 |
| WO | 9404603 A1 | 3/1994 |
| WO | 0075221 A1 | 12/2000 |
| WO | 0114273 A1 | 3/2001 |
| WO | 03001169 A1 | 1/2003 |
| WO | 2006015440 A1 | 2/2006 |
| WO | 2007067140 A1 | 6/2007 |
| WO | 2008012064 A1 | 1/2008 |

OTHER PUBLICATIONS

Database WPI, Week 200921, Thomson Scientific XP002636088, retrieved May 2, 2014.

Donald Alfred Wellings, "Novel Concepts for the design and manufacture of solid supports for synthesis of Peptides", J of Peptide Research and Therapeutics, vol. 16, No. 3 Aug. 4, 2010.

Machine translation of SU617427, retrieved May 2, 2014.

* cited by examiner

Figure 1 cross-linked macroporous polyacrylamide containing hollow polyacrylonitrile spheres
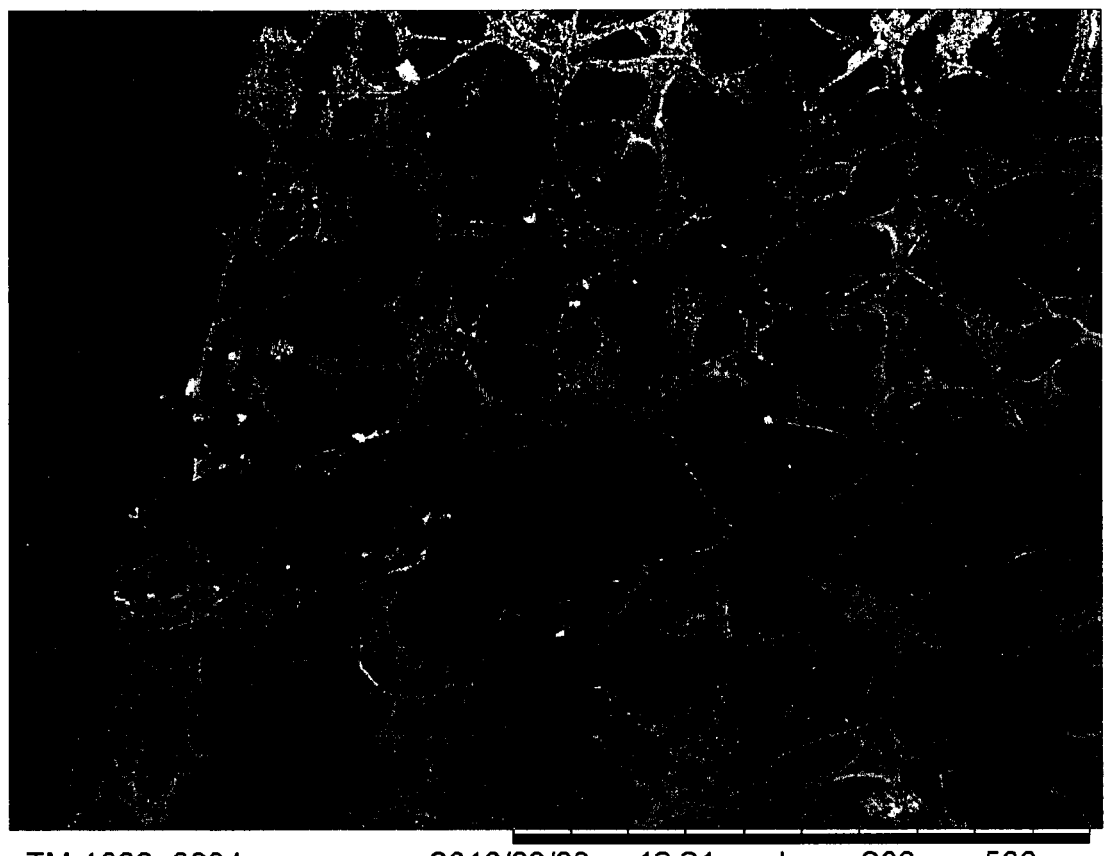

Figure 2 cross-linked macroporous polyacrylic acid
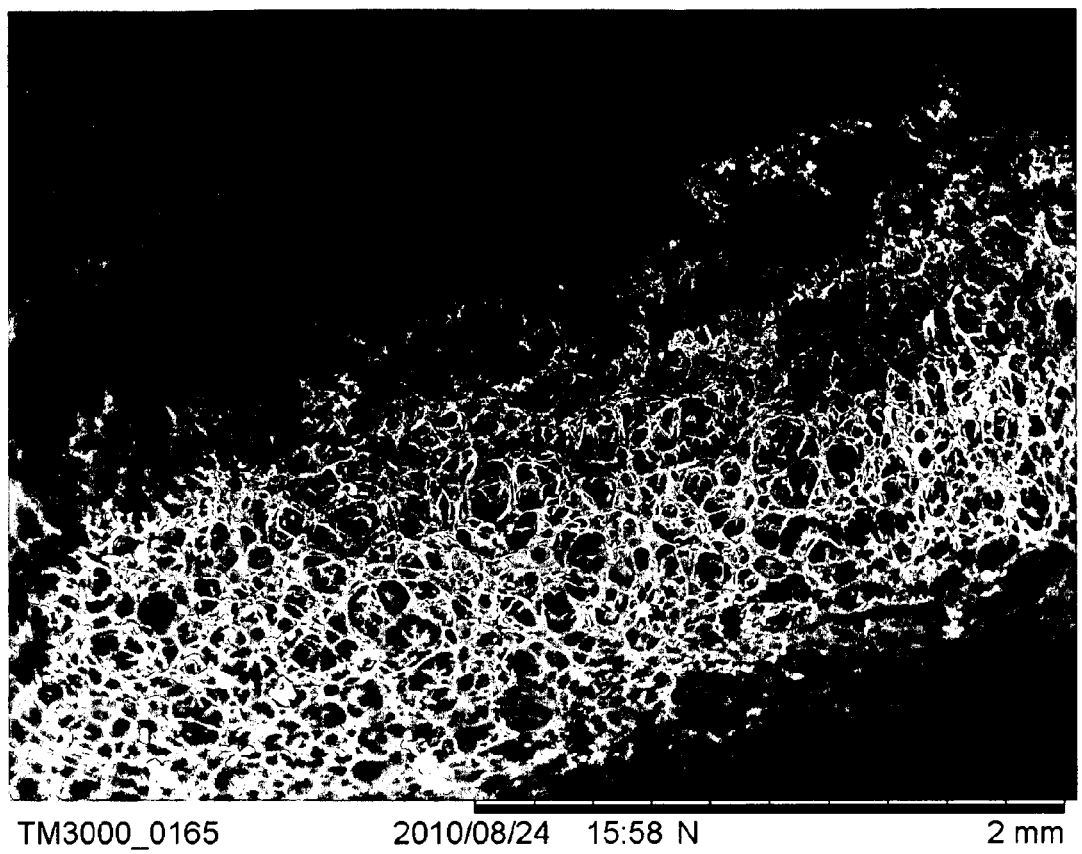

Figure 3 supermacroporous polystyrene
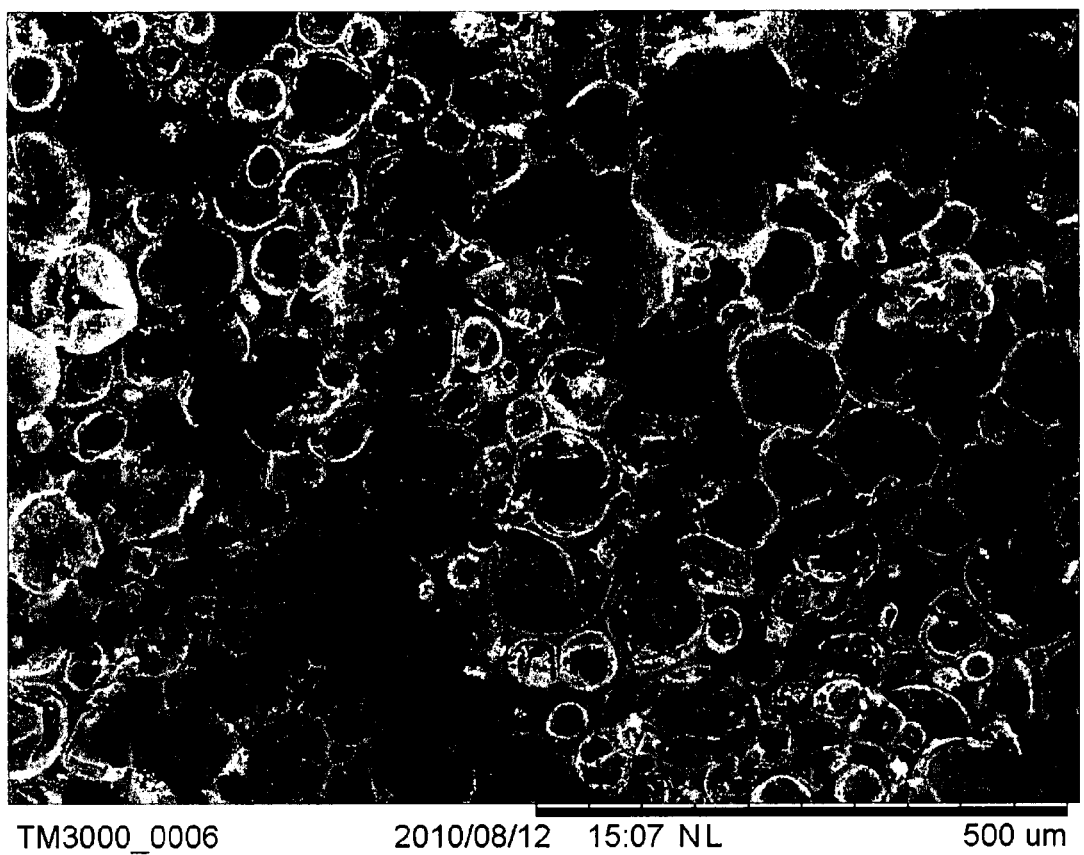

Figure 4 supermacroporous polystyrene containing hollow glass spheres
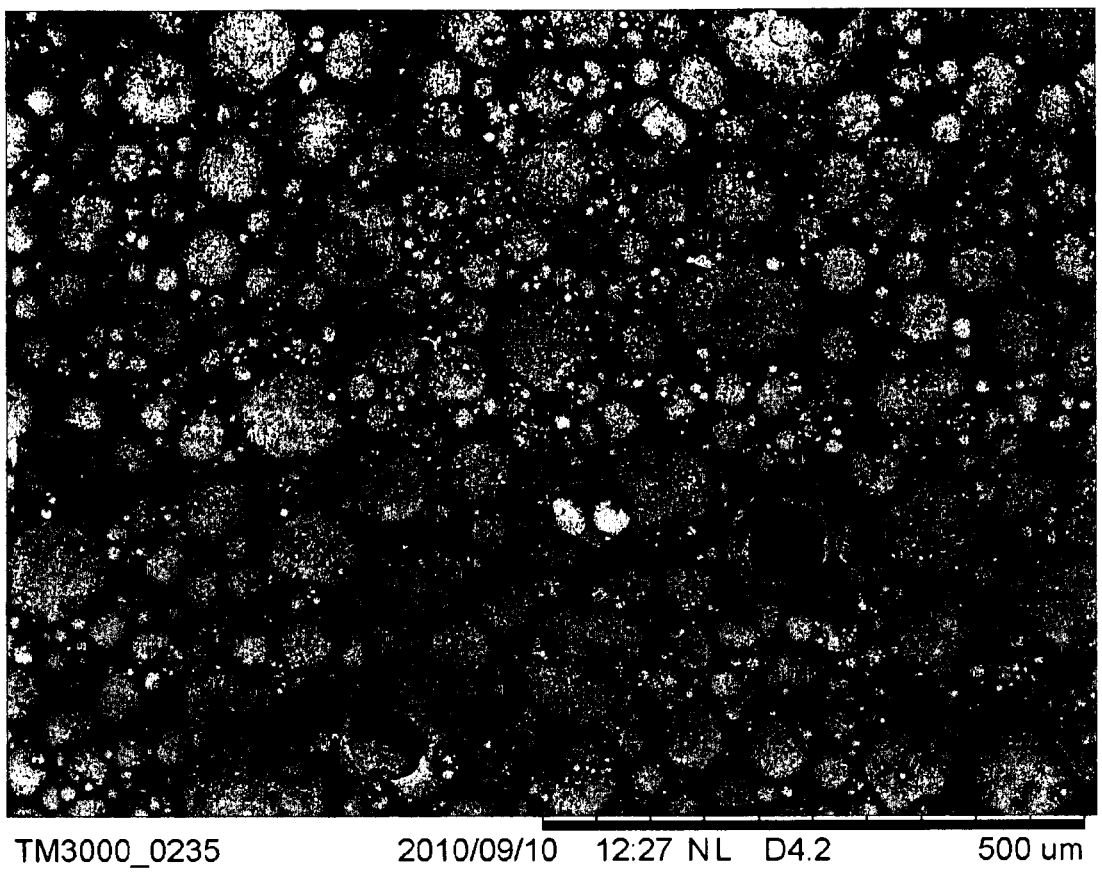
Note: some hollow glass spheres are damaged by sectioning

Figure 5 supermacroporous silica
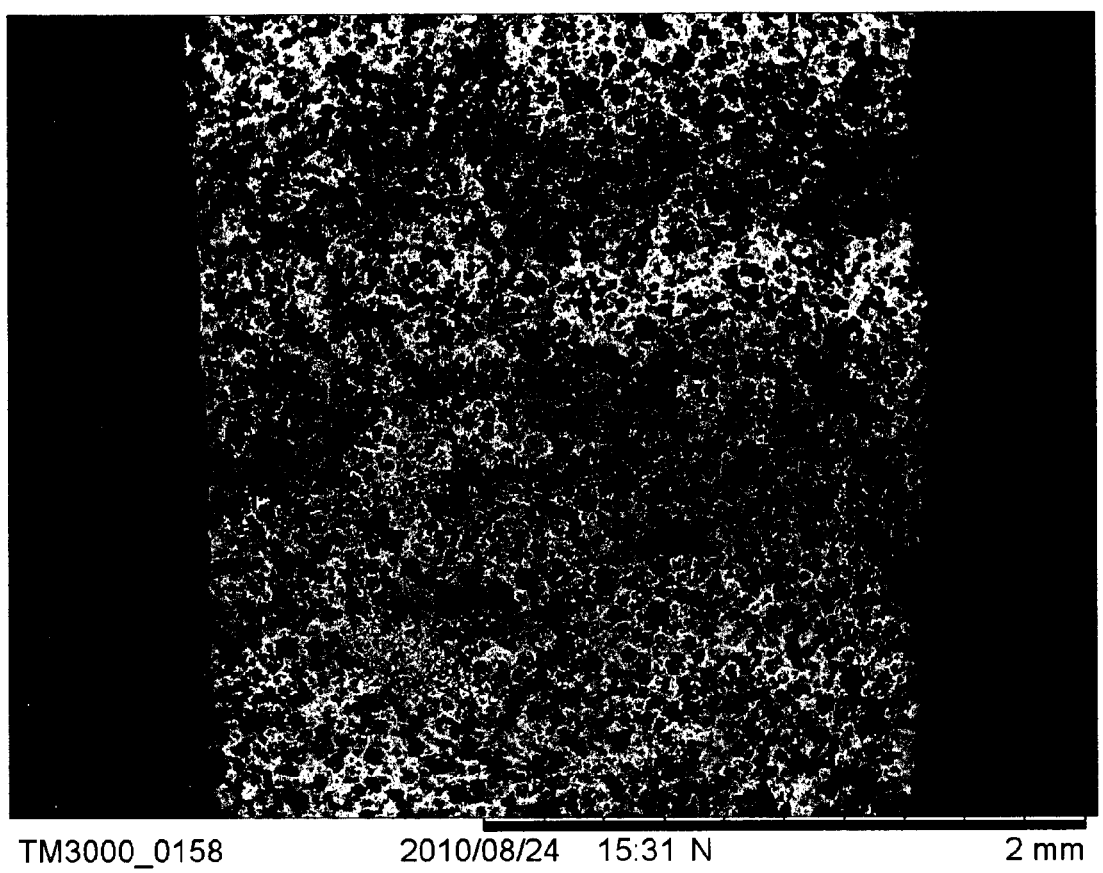

Figure 6 supermacroporous silica
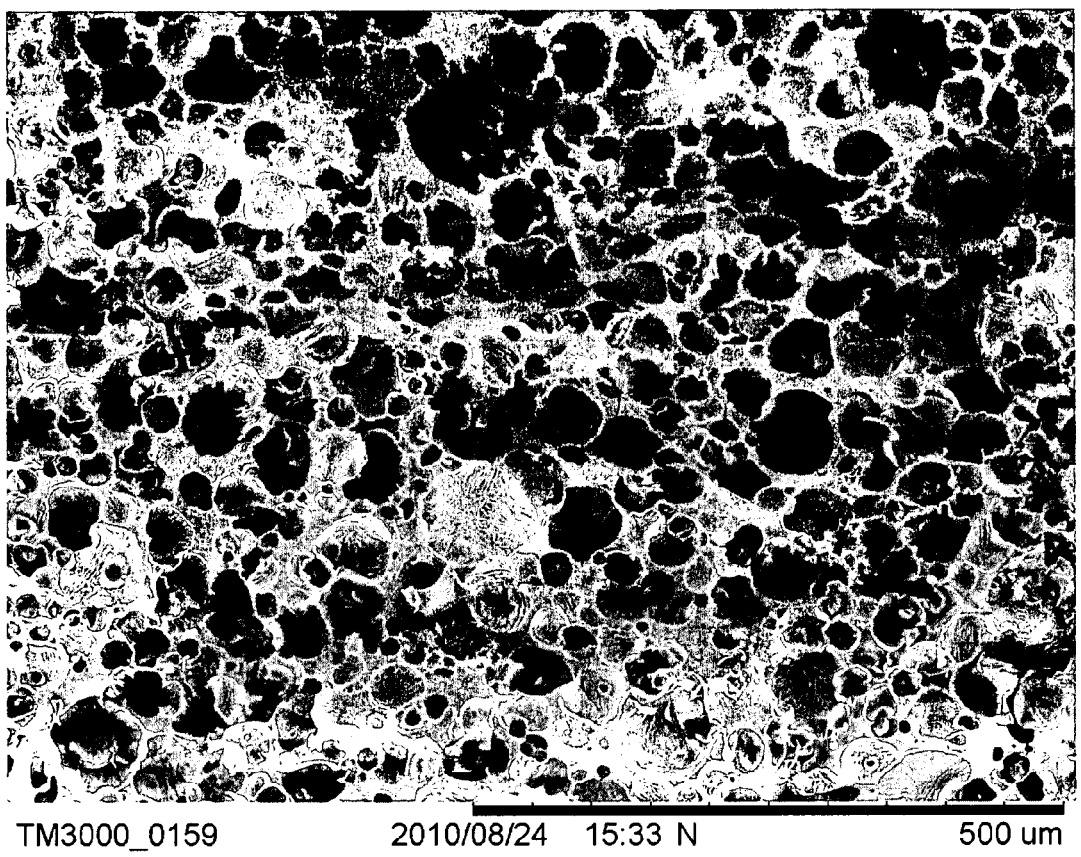

Figure 7 macroporous silica containing hollow glass spheres
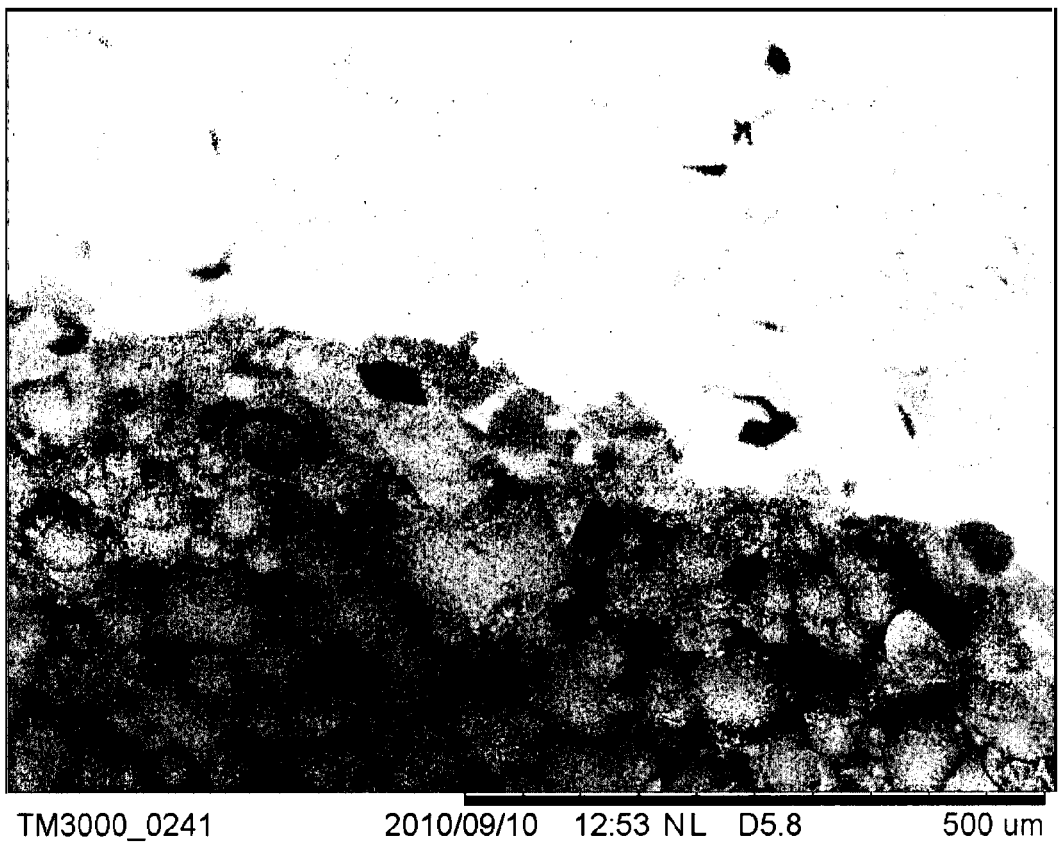
Note: some hollow glass spheres are damaged by sectioning Figure 8 cross-linked 3D macroporous polyacrylamide containing hollow polyacrylonitrile spheres encapsulated within glass seed beads
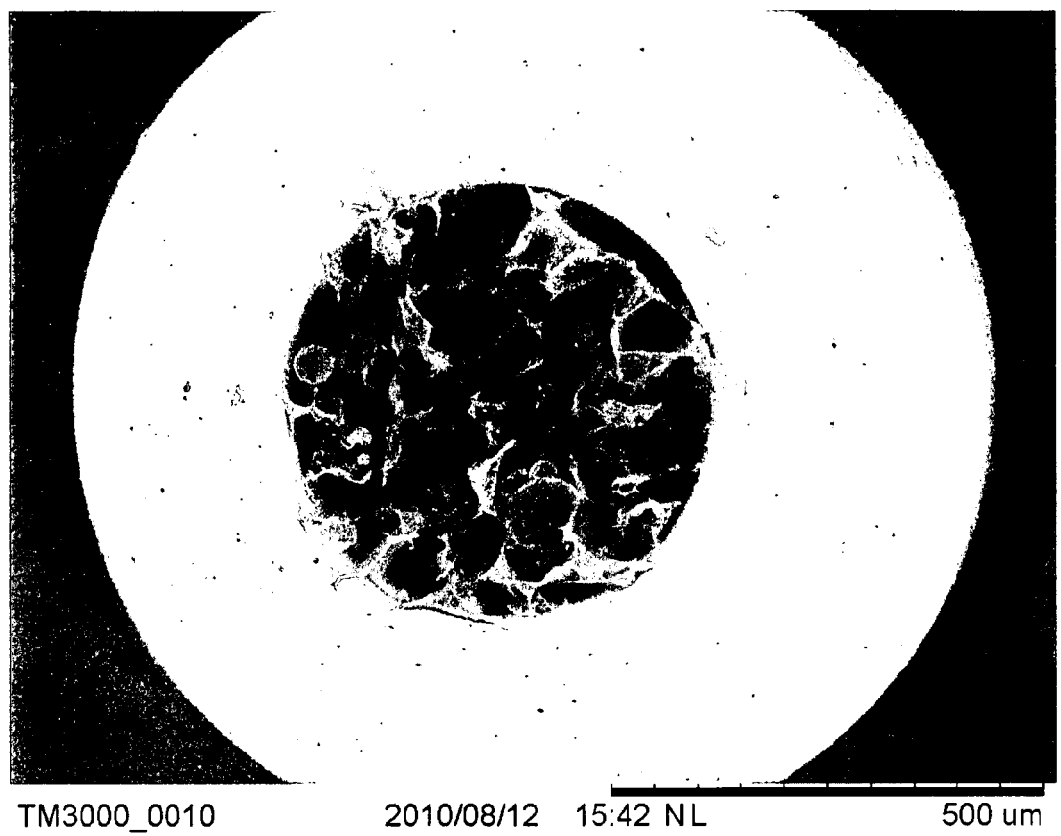

THREE DIMENSIONAL POROUS POLYMERIC STRUCTURE HAVING A PORE-SIZE RANGE OF 1/10 TO 10 TIMES THE AVERAGE PORE SIZE

RELATED APPLICATIONS

This application is a 35 U.S.C. 517 371filing of International Patent Application No: PCT/EP2010/005699, which was filed on Sept. 16, 2010, and which claims priority to Great Britain Patent Application No: 0916281.9, which was filed on Sept. 16, 2009. The entire contents of the aforementioned applications are hereby incorporated herein by reference.

This invention relates to a porous structure, a method of preparing the structure and the use of the structure in a solid phase process. The structure is useful in a wide range of physical and chemical processes especially where interaction with a substrate is required for example solid phase synthesis, solid phase extraction, solid phase reagents, immobilization of species, cell culture, catalysis, chromatography and in medical diagnostics.

Three dimensional macroporous structures have been prepared for a broad range of applications including for example porous monoliths as stationary phases for chromatography, porous discs for filtration of species, porous materials for electroosmotic pumps, solid supports for solid phase synthesis and other chemical transformations, insulating materials, porous membranes for use in fuel cell applications and multi-dimensional scaffolds for tissue engineering. The three dimensional (3D) structures can be made in a range of materials including organic polymers which include for example polystyrene and inorganic polymers which include for example silica.

However, difficulties arise in producing well defined pore dimensions and interconnecting channels in a wide range of polymers. The range of polymers in which reasonable control over pore dimensions may be obtained is limited. There would be significant practical benefit in being able to produce well-defined pore dimensions and channels in a wide range of polymers.

In chromatographic applications the 3D structures are often referred to as monoliths. When monoliths are used for chromatographic applications the 3D structure is employed instead of a traditional particulate stationary phase. The typical driving force for mass transfer within the pores of particulate stationary phases is diffusion. Convective flow through the pores of a monolith enables a substantial increase in the separation speed of large molecules for example proteins as compared to diffusion and. 3D monoliths are advantageous over conventional stationary phases in this regard.

Typically, the monolithic material is prepared in a flat or tubular mould, the sheet or cylinder removed from the mould, and the porous polymer punched or sliced to obtain discs. The pores within these monoliths are incorporated by addition of porogens. In silica based monoliths for example the porogens are typically large molecules such as polyethylene glycols. In polystyrene based monoliths for example the porogens is often toluene. The porogens currently in use introduce a broad pore size distribution with ill defined connectivity which is detrimental to the chromatographic performance of the monoliths.

3D structures used for filtration are often prepared by sintering particles. Glass filters for example are prepared by sintering particulate glass for instance. The porosity of the sinter produced is controlled by the particle size of the starting glass powder which is poorly defined and leads to a broad pore size distribution. These sintered 3D structures may be used in a range of other applications including electroosmotic pumps and the pore size distribution and interconnecting channels of the 3D structures influence the back pressure and flow rate through the pump. If the pore size is too small the flow rate can be high but subsequently the back pressure is also high. The efficiency of these pumps which offer applications for example in fuel cells could be greatly improved by providing a more controlled pore size to facilitate efficient convective flow.

Proton exchange membrane fuel cells, also known as polymer electrolyte membrane (PEM) fuel cells are being developed for a range of applications including transport applications. PEM fuel cells use a polymer electrolyte membrane which desirably allows efficient convective flow through the membrane.

Solid support materials useful in solid phase synthetic processes are known. A wide range of physical and chemical processes employ solid support materials including by way of example synthesis of organic molecules, in particular peptides and oligonucleotides, immobilization of species, support of catalysts, ion exchange, extraction of species from a material, diagnostics and chromatography.

Solid phase synthesis offers some advantages over solution phase synthesis, for example, isolation procedures may be simplified or avoided, reductions in time to carry out procedures may be secured and product may be recovered in essentially quantitative yield. Polymer supports are commonly used for the immobilization of catalysts for use in traditional organic chemistry including chemo and bio catalysis and to immobilize biological macromolecules in medical and diagnostic applications.

The use of 3D structures in solid phase extraction and in the preparation of solid phase reagents is also known in the chemical, pharmaceutical and biotechnology industry.

Known solid phase supports generally comprise polymer particles of a particular size and physical nature to suit the application. For ease of use these polymer particles are often spherical and have a defined particle size distribution. The spherical nature of the particles improves the flow and filtration characteristics of the polymer. Although the uses of solid supports have advantages there are disadvantages to the solid phase approach. For example, commercially available supports commonly used for solid phase synthesis of peptides and oligonucleotides may be expensive, for example due to the complex, manufacturing processes. These processes are disadvantageous in some respects including monomer loss to the continuous phase, generation of a range of particle sizes and the undesirable generation of fine particles during the polymerization and laborious particle size classification, for example sieving and air classification.

In addition to undesirable costs of manufacture and wastage during preparation certain disadvantages may arise with the physical properties of the known polymeric particles. Microporous polymers may be used as supports and have a relatively low level of cross-linker which allows the polymer particles to solvate and consequently swell which may constrain flow pathways. Microporous polymeric particles are generally soft and generally not suitable for use in chromatography applications at a high flow rate in a packed column bed. In addition, the soft particles may be compressed undesirably and cause fouling, for example during filtration often leading to compressive intrusion into the sinter or mesh being used at the bottom of the column. Macroporous polymers have a high level of cross-linker in the polymer matrix and contain large pores rigid macroporous and macroreticular particles are more suited to high flow rates in packed column beds.

However, due to the rigid nature the particles may be fragile and fragment under physical stress.

These problems are exacerbated by conventional column packing techniques in which the polymer particles may be subjected to undesirably large stresses.

In order to culture and differentiate cells in three dimensions it is necessary to seed cells into an artificial structure capable of supporting tissue formation. These structures, usually referred to as scaffolds, are critical for allowing cells to influence their own microenvironments both ex-vivo and in-vivo. The scaffold must firstly allow cell attachment and migration, enable diffusion of cell nutrients and expressed waste and provide the requisite mechanical and biological properties. The porosity and properties under flow are important factors to consider when designing macroporous structures. The macroporous scaffold's utilized to-date have poorly defined pore structure and the pores are generally either too small or have broad pore size distribution. A structure which allows efficient migration of nutrients and waste and allows rapid and unhindered diffusion of cells would be desirable.

Porous polymers are known, however they typically have a wide pore size distribution. It is known to polymerize monomers in an aqueous emulsion in which the polymer forms around droplets of water. A wide range of sizes of water droplet, typically at least an order of magnitude, mean that the pores of the polymer also have a wide size distribution. Further, the water is removed to provide a porous polymer but this does not readily enable material to be left in the voids or pores formed in the polymer.

In a wide range of applications, problems arise due to a wide range of pore sizes and lack of relative uniformity in the dimensions of pathways between pores. The invention aims to ameliorate problems associated with current technologies.

BRIEF DESCRIPTION OF THE DRAWINGS

FIG. 1 shows a scanning electron micrograph of the product prepared according to Example 1.

FIG. 2 shows a scanning electron micrograph of the product prepared according to Example 2.

FIG. 3 shows a scanning electron micrograph of the product prepared according to Example 3.

FIG. 4 shows a scanning electron micrograph of the product prepared according to Example 5.

FIGS. 5 and 6 each show a scanning electron micrograph of the product according to Example 6.

FIG. 7 shows a scanning electron micrograph of the product prepared according to Example 7.

FIG. 8 shows a scanning electron micrograph of the product prepared according to Example 8.

We have now found that these and other problems associated with known polymer particles may be ameliorated by providing a 3D macroporous structure having a narrow pore size distribution. The narrow pore size distribution is obtained by closely packing particles of a particular particle size and filling the interstitial spaces between the particles with a flowable composition, for example a solution of a monomer, and effecting polymerisation of the monomer such that the particles in effect provide a mould for the polymerised mass. On formation, polymers typically shrink whereby pathways are created between the particles and the polymer.

In a first aspect, the invention provides a process for producing a 3-dimensional porous structure comprising closely packing particles in a zone to provide a 3 dimensional array of the particles, contacting a polymerisable monomer, preferably the neat monomer or a composition comprising a polymerisable monomer, with the array such that the monomer or composition comprising a monomer fills interstitial spaces between the particles and effecting polymerisation of the monomer whereby a polymer structure is formed around the particles and optionally removing the particles from the structure.

To create a 3D macroporous structure a plurality of particles can be packed together and the interstitial spaces between the particles filled with a composition containing a monomer which is subsequently polymerised. Depending upon the ultimate application the particles used to form the macroporous structure can be removed by dissolution, chemical degradation, enzymatic degradation, melting or some other process designed to remove the particles and leave the macroporous structure in place or may be retained within the macroporous structure.

The 3D macroporous polymer of the invention may be produced by a polymerisation, initiated by processes known to those skilled in the art. For example, particles mixed with a monomer or a solution of the monomer containing a free radical initiator are heated to effect polymerisation.

In a preferred embodiment, the process for producing the 3D structure comprises forming a slurry of the particles in a liquid wherein the liquid is a composition comprising the monomer or neat monomer. Suitably, the solution comprises a solvent in which the monomer is soluble for example water or toluene depending on the hydrophilicity of the monomer. Preferably the slurry is concentrated so as to keep the liquid component to a minimum required to fill the interstitial spaces between the particles as they are packed together. In hexagonal close-packing, the interstitial space is calculated at around 24% of the volume and suitably the liquid component would be present at not more than 30% and preferably 24 or 25% to fill the interstitial gaps and have a small quantity left for lubrication between the particles to facilitate movement into a close packing arrangement. Increasing the level of the liquid component in the slurry may alter the structure of the 3D structure and provides scope for the user to tailor the conditions as desired.

The particles may be hollow and buoyant in the liquid. In this case, a larger amount of liquid component may be employed so the particles float and pack closely at the surface of the liquid.

Upon contacting the liquid and particles, polymerisation is initiated in a conventional manner depending on the monomer employed. A free radical initiator or catalyst may be added to the liquid component to initiate or effect polymerisation.

In a second aspect, the invention provides a 3-dimensional porous polymeric structure comprising a porous polymer structure optionally with particles within the pores of the polymer and wherein the pores have a narrow pore-size distribution.

The porous polymer of the 3D structure may be any inorganic or organic polymer. Examples of suitable polymers include polyacrylamide, polyacrylic acid, polystyrenedivinylbenzene, silica, polystyrene, cellulose, agarose, polydimethylacrylamide, polymethylmethacrylate, polymethacrylate, polyacrylate, polyurea, polyacryloylmorpholine, polyvinylalcohol, silica, polybetahydroxy ester and polyacrylonitrile.

Preferably the pores in the structure are such that the structure has a pore size range from between 1/10 to 10 times the average pore size in the structure, more preferably between 1/5 to 5 times, desirably between 1/2 and 2 times the average pore size diameter. Optimally the pore size range is from 75 to 125% and especially from 90 to 110% of the average pore size diameter.

Suitably, the pore sizes in the 3D structure are measured using scanning electron microscopy although other known methods may be employed as desired.

In plotting a graph of pore size versus occurrence of the pore size within a structure, known porous polymers would typically show a wide "bell-shape" Gaussian distribution whereas the structures of the present invention would show a much narrower "spike" to demonstrate the narrow pore size distribution.

The 3-dimensional structure may retain the particles within the pores of the polymer structure or the particles may be removed once the polymer structure is formed. On polymerizing the monomer from the composition, the formed polymer will retreat from the particles due to the polymer shrinking on formation as compared to the interstitial space occupied by the composition. This shrinkage creates labyrinthine pathways between the interstices which may be utilised in applications to provide relatively uniform flow through the polymer structure. The particles may then be left in situ optionally to perform further functions or may be removed to leave the porous 3D structure with pores in the space previously occupied by the particles which are linked by the pathways between interstices.

In a preferred embodiment, the 3D structure, which may be referred to herein as a "scaffold", may comprise polymer particles or a continuous polymer gel entrapped within the macroporous structure. Alternatively the 3D structure itself without anything in the pore may be used depending on the application.

Advantageously, the invention provides a means of producing novel 3D structures with a narrow pore size distribution in a relatively inexpensive manner and provides 3D structures which may be adapted for use in a wide range of applications with chemical and physical characteristics that have not been previously achievable.

The term "polymer" as employed herein includes inorganic polymers, for example silica and organic polymers, for example polystyrene. Polymeric particles may typically be made by a dispersion or emulsion polymerization process in which a solution of monomers is dispersed in an immiscible solvent (continuous phase) prior to initiation of the polymerization. The polymer particles formed are typically then filtered, washed and classified to isolate the required particle size distribution.

The terms "macroporous" and "supermacroporous" as employed herein are not used in a limitative sense as regards the size of pores or degree of porosity or otherwise. The 3D structures of the invention are porous and the generality of this term is not limited by the use herein of the terms "macroporous" and "supermacroporous".

The particle may be any suitable material capable of forming a close-packing arrangement and which has a relatively uniform particle size. In a preferred embodiment the particle is preformed from glass or polymer. Cells may also be used as particles to define the pore size of the 3D structure. The particle may be hollow or solid. Hollow glass particles and hollow polymer particles are widely available and commonly used in many industries and have applications including road markings, explosives, cosmetics and building materials. Advantageously, they are manufactured on a large scale are not costly and are available in a wide range of dimensions and of acceptable physical and chemical characteristics.

The particle used to form the 3D structure can be any suitable material but advantageously comprises an inexpensive readily available material.

The pore size of the 3D structure is dictated by the particle size and may be from sub-micron size to the millimeter scale, for example 0.1 µm to 1 mm. By way of example, yeast cells (baker's yeast) may be used to generate small pores, for example 1 to 10 µm, spherical wax particles used in the coatings industry can be used to generate slightly larger pores in the range 5 to 50 µm. Glass and polymer particles are available in a wide range of sizes allowing selection of the desired particle size to create pores having a size of 1 to 500 µm, especially 10 to 300 µm. The important consideration is that the particles have a narrow size distribution as this determines the pore size of the 3D structure.

The invention also envisages a 3D porous structure wherein two or more particles of different particle size but each with a narrow particle size distribution are employed. The polymer structure may be formed around the larger particles and the smaller particles will occupy locations in the interstitial space or pathways between them. The 3D porous structure may comprise a polymer structure with larger pores wherein the polymer body defining the pores itself also contains smaller pores.

Suitably, the particulate support of the current invention is spherical, near to spherical or ellipsoidal. The spherical nature of the support is advantageous in many applications and facilitates formation of a more ordered close packing around which to form the 3D structure. However, irregular, oval and other shapes of particle can be used.

There are many grades of hollow glass and hollow polymer particles available which vary in outer diameter and inner diameter that is the diameter of the inner wall of the shell. The particle sizes available include small particles with a mean diameter in the region of 10 µm and larger particles with much larger mean particle diameters in the region of 200 µm. These different grades will be useful for specific applications, for example particles having a size in the region of 10 µm will be useful in preparation of monoliths for high pressure liquid chromatography and particles having a size in the region of 200 µm particles will be useful in creating 3D scaffolds for Stem Cell culture.

Advantageously, the 3D porous structure is buoyant when it is produced using hollow particles. The density of each grade of hollow particle is readily controlled and varied by the ratio of inner diameter to the outer diameter of the hollow particle. The higher this ratio the less dense and more buoyant the final product will be.

Suitable hollow glass particles may be obtained commercially, for example from Potters Industries Inc, Malvern, Pa., USA. Suitable hollow polymer particles may be obtained commercially, for example from Akzo Nobel, Expancel, Box 300, S-850 13, Sundsvall, Sweden and are sold under the trademark Expancel®.

WO2008/012064 describes a solid support comprising a polymer-impregnated bead wherein the bead has a hole in it and the polymer is disposed in the hole. The bead is solid throughout and acts as a framework to support the polymer in the hole. In producing the solid support, the polymer is said to be formed on the bead and in the hole and the polymer on the outside of the bead is removed for example by abrasion.

In a further aspect, the invention provides a solid support comprising a bead having a hole in it and a 3D structure according to the present invention disposed in the hole. The bead is solid throughout and acts as a framework to support the 3D structure in the hole. In producing the solid support, the 3D structure may be formed on the bead and in the hole and the 3D structure on the outside of the bead is suitably removed. Beads comprising 3D macroporous structures according to the invention improve convective flow and mass transport.

Suitably the particle surface can covalently modified for use in certain applications. Also a polymer may be used to coat the outside of the particle. The polymer may be bound covalently to the particle directly or indirectly. Where the particle is made of a material having active sites, the polymer may be bound directly. Where the particle is made of a more inert material, for example glass, it may be desirable to treat the particle to provide active sites to which the polymer may bind. Where the particle comprises glass it is suitably treated with hydrogen fluoride based solution to provide active sites suitable for reaction with a derivative. Where the particle comprises polymer then any suitable chemical reaction can be used to modify the surface. For example, treatment of a hollow polyacrylonitrile based polymer sphere with lithium aluminium hydride will afford primary amine functionality at the surface.

The polymer may be any suitable material according to the desired application. In a preferred embodiment, the polymer is selected from a range of polymer types including but not limited to polyacrylamide, polystyrene, cellulose, agarose, polydimethylacrylamide, polymethylmethacrylate, polymethacrylate, polyacrylate, polyurea, polyacryloylmorpholine, polyvinylalcohol, silica, polybetahydroxy ester and polyacrylonitrile.

The polymer may be reacted further to provide particular functionality for a given application. Suitably, the polymer is reacted with a compound having at least two functional groups, one for reacting with the polymer and the other to provide free functionality for use in the desired application. In a preferred embodiment, the polymer, for example polydimethylacrylamide and polyacryloylmorpholine copolymers with N-acryloyl sarcosine methyl ester, is reacted with a diamine compound, for example ethylene diamine. Amine functionalised supports for example are suitable for use in peptide synthesis, oligonucleotide synthesis, solid phase organic chemistry, enzyme immobilisation and cell culture.

An amine functionalised support may be further functionalised, for example by conversion to a carboxylic acid using succinic acid as desired. By way of example, an amine functionalised support may be treated with N-hydroxysuccinimide and 1-Ethyl-3-[3-dimethylaminopropyl]carbodiimide hydrochloride in preparation for immobilising a protein, for example protein A.

In a further embodiment, the support comprises the particle and a polymer which itself is a macroporous polymer. An especially preferred inert material is PolyHIPE. PolyHIPE is porous and highly absorbent. This material is particularly preferred for applications in which a material is to be absorbed by the 3D macroporous polymer.

In another embodiment, the support comprises the particle and a polymer which itself is a macroporous polymer in which the pores are formed by a traditional porogen. This material is particularly preferred for applications in which a material is to be absorbed by the 3D macroporous polymer.

A 3D macroporous polymer according to the invention may also comprise a functional material supported by the polymer. Examples of suitable functional materials include a catalyst, an initiator species for peptide synthesis, a pharmaceutical active, an agrochemical active, a macromolecule, an enzyme, a nucleic acid sequence and a protein.

The invention is particularly useful in supporting precious metal catalysts, for example palladium catalysts. A particular advantageous example is palladium acetate supported on polyurea.

If preferred the 3D macroporous polymer may be covalently linked to the support particle either during the polymerization or subsequent to the polymerization. Alternatively, one or more of the constituent monomers can be covalently linked to the particle surface prior to initiation of the polymerization.

The 3D macroporous polymer of the invention may be used in any chemical or physical process in which a solid support is used.

The 3D macroporous polymer may be employed in applications involving electro-conducting and light emitting polymers. The particulate support containing light emitting polymers may be arranged on display panels.

The 3D macroporous polymer is particularly useful for solid phase synthesis of an organic species, particularly macromolecules. In a preferred embodiment the 3D macroporous polymer may be employed in the synthesis of peptides, oligonucleotides or oligosaccharides. Polydimethylacrylamide, polyethylene glycol and polystyrene are examples of the polymer support that are particularly advantageous in synthesis of peptides.

In solid phase synthesis, the process for using solid polymeric particles in applications such as peptide synthesis typically involves suspending the particles in the appropriate solvent above a porous filter plate and stirring the particles gently so as not to mechanically damage the particles. Known particles are dense and settle on to the filter in the solvents commonly used. The manufacturing process for the particles often generates fines that cause blockages in the filter plate leading slow filtration or the need to replace or clean the filter. In addition, the stirring of solid particles may cause fracture leading to generation of fines that exaggerate the problems of filter blockage.

In the pharmaceutical and associated industries strict quality regulations under current good manufacturing process (cGMP) require that the filter plate is replaced following each batch of product in order to avoid contamination of subsequent batches with material dislodged from the filter plate.

The 3D macroporous polymer according to the invention simplifies solid phase synthesis through the use of simpler equipment than conventionally employed. The 3D macroporous polymer can be used itself in monolithic form in a column based system. In this instance the polymer forming the 3D macroporous polymer provides the support for solid phase synthesis.

If the 3D macroporous polymer is formed around a traditional polymer support for solid phase synthesis the 3D macroporous polymer can be inert and merely provide a mechanical skeleton to support the traditional polymer for solid phase synthesis.

In the two examples described above the 3D macroporous polymer can be encapsulated within seed beads as described in patent WO2008/012064.

The invention further provides for the use of a 3D macroporous polymer according to the invention as a monolith in a chromatography process.

The application of solid supports or stationary phases in chromatographic separations is very extensive for example complex high-technology separations used in the pharmaceutical and biotechnology industry and larger scale processes used in the mining industry. Some of the pharmaceutical industry's most valuable drugs are purified by preparative chromatography and improved chromatographic separation would be technically beneficial and economically advantageous. In the mining and precious metal recovery industry a large portion of the world's palladium, a critical component in a wide range of industrial applications and processes including catalytic converters and manufacture of high value products, may be refined using immobilized crown ethers (Traczyk, F. P.; Bruening, R. L.; Izatt, N. E. "The Application of Molecular Recognition Technology (MRT) for Removal and Recovery of Metal Ions from Aqueous Solutions"; In Fortschritte in der Hydrometallurgie; 1998, Vorträge beim 34. Metallurgischen Seminar des Fachausschusses fuer Metallurgische Aus-und Weiterbildung der GDMB; 18-20 November 1998; Goslar). The present 3d structure may be employed in these applicaitons.

In a monolithic column for applications in chromatography or solid phase synthesis of, for example peptides, oligonucleotides, catalysis (chemical and biological) uniform flow is highly desirable so that the band of material applied to the column flows uniformly and in a narrow band as it flows through the column. This narrow band is important for chromatographic separations for separation of the components of a mixture, for reaction chemistry where a reagent may be passed through a column to maintain a high concentration at the points of reaction as the band passes down the column. The 3D structures of the invention having relatively narrow pore size distribution are especially useful in providing for relatively uniform flow rates.

Known porous materials, for example polyHIPE, give rise to a relatively broad band on leaving a chromatography column due to the wide range of pore sizes within the material so that in the smaller pores the band would have a more tortuous path and in the larger pores the band would travel much more rapidly. In the present invention, the band travels at a more constant speed due to the narrow pore size distribution.

J J van Deemter developed an equation to define the different types of flow through a column containing a packed bed J J van Deemter (van Deemter, J. J, Zuiderweg, F. J. and Klinkenberg, A. *Chem. Eng. Sci.*, (1956) 5, 271-289) and developed a process for designing the optimum flow rate through a packed bed by plotting flow rate versus column efficiency in terms of band broadening. The 3D structure of the present invention advantageously provides for minimal band broadening.

Conventionally, chromatography columns are generally packed by preparing a slurry of the particles, or stationary phase in a suitable solvent and transferring this into the column. Uneven settling of the bed in chromatography columns can cause uneven and even cracked stationary phase beds resulting in poor and irreproducible separations. Columns often have to be emptied and repacked several times to achieve the required performance. This can be laborious and leads to down time which a particular disadvantage in process scale operations.

The 3D macroporous polymer of the invention provides a reproducible stationary phase for chromatographic separations in the form of a monolith or other suitable media such as a disc that can be used directly as an or encapsulate as described in patent WO2008/012064 for packing in traditional columns.

The 3D macroporous polymer of the invention is also useful for solid phase extraction to remove species from a liquor which is contacted with the support, whether in batch form or as a flow over the 3D macroporous polymer, for example ion extraction and ion exchange. Solid phase extraction is typically performed in columns or in systems with filter plates for separation of the solid phase from the mixture under extraction. The problems observed for solid phase synthesis and chromatography referred to herein may similarly be observed with solid phase extraction. The 3D macroporous polymer of the invention provides similar advantages as afforded in chromatography and solid phase synthesis.

The 3D macroporous polymer of the invention may be used to immobilize species including antibodies, oligonucleotides, enzymes, whole cells or fluors and may be positioned in an array, with each 3D macroporous polymer in the array is used to assay a different component of a solution. 3D macroporous polymers having ligands covalently attached to their surface, or via polymers bound to the surface may be employed in 'wells'. Specific binding of a target ligand such as antigen or complimentary DNA or RNA sequence may then be detected using established methods. Immobilized enzymes may be employed to perform organic chemical reactions or for chiral resolution, for example the use of immobilized Penicillin amidase for the resolution of secondary alcohols (E. Baldaro et al. Tet. Asym. 4, 1031, (1993) and immobilized Penicillin G amidase is also used for the hydrolysis of Benzylpenicillin in the manufacture of Amoxicillin (Carleysmith, S. W. and Lilly, M. D. Biotechnol. Bioeng., 21, 1057-73, 1979).

The 3D structure of the invention is also useful in immobilizing biological macromolecules for medical and diagnostic applications. This includes immobilization of proteins, monoclonal and polyclonal antibodies. Cell culture is commonly carried out on solid supports with specific surface characteristics and morphology. Immobilized enzymes in the particles may be employed as sensors to generate a signal. An example is the detection of glucose by the glucose oxidase/peroxidase coupled enzyme system, in which the presence of glucose generates hydrogen peroxide which in turn is the substrate for peroxidase for the oxidation of a wide variety of substrates to provide a coloured, fluorescent or luminescent signal.

The 3D macroporous polymer of the invention also may be employed to immobilize a biocatalyst. Biocatalysts are often used in columns or in systems with filter plates for separation of the solid phase from the mixture under extraction. The problems observed for solid phase synthesis and chromatography referred to herein may similarly be observed with solid phase extraction. The 3D macroporous polymer of the invention provides similar advantages as afforded in chromatography and solid phase synthesis.

Conventionally immobilized biocatalysts, for example immobilized enzymes, on solid supports may disadvantageously settle on the base of the reactor leading to reduced contact of the biocatalyst with the substrate. The particulate support of the present invention may be used in monolithic or particulate form to ensure the maximum usable area of the biocatalyst remains available to the substrate.

The present invention also envisages systems with two or more different immobilized biocatalysts or cofactors in the same column or reactor. In this invention one entity could be immobilized on the 3D macroporous polymer and the other upon the spherical particles used to create the structure.

The 3D macroporous polymer of the invention is especially useful in immobilising species including solid phase reagents, metal and other catalysts, bio-catalysts, enzymes, proteins, antibodies including polyclonal and monoclonal antibodies, whole cells and polymers. The invention is particularly advantageous in supporting enzymes, for example the lipase Cal A works well, particularly in combination with polydimethylacrylamide and other similar hydrophilic polymers. The lipase Cal B is commonly employed in the manufacture of biodiesel and works well supported upon hydrophobic polymers such as polystyrene. Moreover the improved convective flow through the 3D macroporous polymer structures of this invention may be particularly suited to the flow of viscous vegetable oils throughout the matrix and therefore find particular application for biodiesel manufacture.

The present invention is also especially useful in the immobilisation of affinity ligands, such as Protein A which used in the industrial scale purification of biopharmaceuticals.

In a further application, the particulate support of the invention may also be used in chemocatalysis, for example by immobilizing transition metal catalysts and ligands.

In yet a further application, the present invention may be used in cell culture. Mass culture of animal cell lines is fundamental to the manufacture of viral vaccines and many products of biotechnology. Biological products produced by recombinant DNA technology in animal cell cultures include enzymes, synthetic hormones, immunobiologicals (monoclonal antibodies, interleukins, lymphokines) and anticancer agents. Many simpler proteins can be produced using rDNA in bacterial cultures; more complex proteins that are glycosylated (carbohydrate-modified) currently must be made in animal cells. An important example of such a complex protein is the hormone erythropoietin. The cost of growing mammalian cell cultures is high, so companies are constantly looking to improve techniques.

Cells can be grown in suspension or as adherent cultures. However, adherent cells require a surface, which may be coated with extracellular matrix components to increase adhesion properties and provide other signals needed for growth and differentiation. Generally cells derived from solid tissues are adherent. Organotypic culture involves growing cells in a three-dimensional environment as opposed to two-dimensional culture dishes. This 3D culture system is biochemically and physiologically more similar to in vivo tissue, but is technically challenging to maintain because of many factors (e.g. diffusion).

In a further aspect, the invention provides a process for the continuous production of monoclonal antibodies or other bioactive molecules secreted or excreted by cells of simple or complex nature, or cell-free systems in which the production unit is grown on or otherwise attached reversibly or irreversibly to a 3D structure according to the invention.

In another embodiment the interstitial spaces between the particles forming the 3D macroporous polymer may be filled with additional components such as a cell culture nutrient for example. In this example the cells may be cultured on the polymer particle used to form the 3D macroporous polymer or on the 3D macroporous polymer itself. Suitably the 3D structure is contained or cast within a retaining device, for example a sleeve, cassette or may be formed into a desired shape and materials, for example in the form of a solution or a vapour comprising nutrients or other active components may be contacted with the 3D structure for example by passing onto, over or through the porous structure. The 3D structure of the invention is suitable for use as a production unit for organic bodies, for example stem cells, organs and bone and in tissue engineering.

Advantageously, waste material for example containing secreted or excreted materials may be removed efficiently and without destroying, damaging or limiting the efficiency of the production unit. Suitably the retaining device is impermeable, semi-permeable or permeable to allow for the introduction and removal of active components and waste materials.

The 3D structures of the invention may also be employed in a process for the production of two or more shaped surfaces of matrices comprising the 3D structure. Suitably the matrices may comprise the same or different polymers and preferably are cast or extruded to the desired shape. The matrices suitably have similar or different pore sizes, a gradation of pore sizes, or spatially separated pore sizes.

Cells of human or non-human origins, or cell-free components may be seeded into one or all surfaces in an adjacent, contiguous or spatially separated way. The intention of the process is to investigate by any biochemical or morphological means the biological, biochemical and biophysical characteristics of cells as individuals or populations, and their interaction.

The invention also provides for the use of the 3D structure as a construct for cell culture and regenerative medicine. The invention allows tissue to be created in order to repair or replace existing organs or body parts for example repairing a damaged muscle to growing a whole human organ for example a kidney and a heart and replacing bone.

The 3D structure of the invention provides a supermacroporous structure in which to grow and differentiate the cells. The narrow pore size distribution in the 3D structure enables relatively uniform flow of cells, nutrients and waste through the structure. Use of appropriate size particles allows the user to determine the pore size across the 3D structure according to the specific application. For example bone is not uniform throughout its entire length and use of two or more different sizes of particle, each different size of particle having a narrow particle size distribution enables tailoring of the 3D structure to provide bone of different density or porosity to mimic original bone structure.

The 3D structures of the present invention may also be used in other biological applications including use as cast or extruded matrices for the collection of air-borne organisms under negative or positive pressure. Application of the 3D structure to chips and/or optical fibres as biosensors, and for use in wound or burn management as a custom-moulded, inert surface wound/burn, protection/closure for example for fingers, arms, feet; veterinary use, for the local application of a therapeutic agent, for example topical antiseptic, antibiotic, antifungal preparations through the closure, and allowing for the exchange of air.

The invention described herein allows for a more precisely controlled pore structure, pore volume, pore connectivity and pore dimension than could previously be achieved for tissue engineering. The process allows for the manufacture of 3-D structures in practically any polymer including biodegradable, biocompatible, organic or inorganic. These 3D macroporous polymer structures, commonly referred to as supermacroporous when pores of greater than 100 μm are created, are amenable to rapid cell and nutrient migration under static and convectional conditions. The 3D macroporous polymer structures of this invention can be manufactured or cast in almost any shape or size and therefore provide an important scaffold for regenerative medicine.

In a further aspect, the invention therefore provides for the use of a 3D macroporous polymer according to the invention to culture cells on the surface of the pores or on the surface of the spherical particle used to create the pores. Suitably, stem cells may be cultured on the particulate support of the invention to reduce uncontrolled differentiation and to control desired differentiation. The handling characteristics of the particulate support and high utilization of surface area and pore diameter of the 3D macroporous polymer are advantageous in this application.

The invention is particular useful in medical diagnostic tests such as immunoassay. Accordingly the invention further provides medical diagnostics for detecting the presence of a compound comprising a particulate support according to the invention and a functional material such as an enzyme, for example horseradish peroxidase, supported by the polymer in the support for selectively reacting with or binding to the compound to be detected.

Many medical diagnostics rely upon solid supports to immobilize various diagnostic ligands. The 3D macroporous polymer of the present invention may be used in a medical diagnostic procedure where physical separation of the solid phase through a liquid phase.

In a further application, the 3D macroporous polymer may be used as an absorbent. In this application, it is especially advantageous if the 3D macroporous polymer is an inert, absorbent material. PolyHIPE is a particularly preferred inert material. The 3D macroporous polymer may be used to absorb household spillages, for example tea, coffee and wine, or may be used in larger-scale applications for example, to absorb oil from spillages. The absorbent support may be used to absorb the spillage and then physically removed or, in the case of oil spillage in a body of water, effectively trap the oil and retain the oil in a buoyant mass for collection and disposal.

The 3D macroporous polymer of the invention may be used as a carrier to carry a compound which is to be released over a period of time, for example a pharmaceutical or agrochemical compound or composition. This use provides a means of tailoring a dosage regime of the compound according to the loading of the compound in the support. In the case of a pharmaceutical, this may be advantageous in assisting the correct dosage of an active, for example with continuous slow release rather than requiring a patient to take periodic large doses, for example in chemotherapy.

The invention is illustrated by reference to the examples and the accompanying scanning electron micrographs (SEM's). These are referred to in the listed examples.

EXAMPLES

Example 1

Encapsulation of Expancel 920 DEX 80 d30 in Polyacrylamide

Methylene-bis-acrylamide (MBA) (123 mg, 0.8 mmol) was dissolved with warming in N,N-dimethylformamide (DMF) (1.26 cm$^3$). This solution was cooled to room temperature and 2-(dimethylamino)ethylmethacrylate (DMAEM) (0.43 cm$^3$, 0.55 mmol), acrylamide (2.02 g, 28.5 mmol), tetramethylendiamine (TEMEDA) (0.006 cm$^3$, 0.05 mmol) and water added.

The mixture was agitated until all components dissolved. Expancel 920 DEX 80 d30 (80 μm polyacrylonitrile balloons) (150 mg, 10 cm$^3$) was added and mixed thoroughly before ammonium persulfate solution (0.285 cm$^3$ of 1% w/v) was added to initiate polymerisation. The mixture was cast into discs in a Teflon moulds. The polymerisation was left to go to completion overnight at room temperature then washed thoroughly with water before freeze drying.

A scanning electron micrograph (SEM) of the product is shown in FIG. 1.

Example 2

Preparation of Polyacrylic Acid

Methylene-bis-acrylamide (MBA) (240 mg, 1.55 mmol) was dissolved with warming in N,N-dimethylformamide (DMF) (2.5 cm$^3$). This solution was cooled to room temperature and 2-(dimethylamino)ethylmethacrylate (DMAEM) (0.43 cm$^3$, 0.55 mmol), acrylamide (1.9 g, 26.8 mmol), tetramethylendiamine (TEMEDA) (0.006 cm$^3$, 0.05 mmol) and water added. The mixture was agitated until all components dissolved. Expancel 920 DEX 80 d30 (80 μm polyacrylonitrile balloons) (150mg, 10 cm$^3$) was added and mixed thoroughly before ammonium persulfate solution (0.285 cm$^3$ of 1% w/v was added to initiate polymerisation. The mixture was cast into discs in a Teflon moulds. The polymerisation was left to go to completion overnight at room temperature.

Several of the discs prepared above were treated with aqueous sodium hydroxide (20% w/v) at 80-100° C. until the polymer matrix became clear. The discs were washed thoroughly with dilute hydrochloric acid (1 mol/dm$^3$) and water before freeze drying.

An SEM of the product is shown in FIG. 2.

Example 3

Preparation of Polystyrene-Divinylbenzene 1,4-Divinylbenzene (DVB) (4.6 cm$^3$, 43 mmol), styrene (0.92 cm$^3$, 8.85 mmol) and 1,1-azobis(cyclohexane-carbonitrile) (100 mg) were added to Expancel 920 DEX 80 d30 (150 mg, 10 cm$^3$) and mixed thoroughly. The mixture was cast into discs in a Teflon moulds. The polymerisation was left to go to completion overnight at 80° C. temperature. The discs were washed thoroughly with diethyl ether and air dried.

Several of the discs prepared above were treated with DMF at 80-100° C. for several hours before washing thoroughly with diethyl ether and air drying.

An SEM of the product is shown in FIG. 3.

Example 4

Polydimethylacrylamide Particles Encapsulated in Polystyrene-Divinylbenzene 1,4-Divinylbenzene (DVB) (0.934 cm$^3$, 8.7 mmol), styrene (0.19 cm$^3$, 1.83 mmol), toluene (1 cm$^3$) and 1,1-azobis(cyclohexane-carbonitrile) (50 mg) were added to Expancel 920 DEX 80 d30 (150 mg, 10 cm$^3$) and mixed thoroughly. The mixture was cast into discs in a Teflon moulds and the polymerisation was left to go to completion overnight at 80° C. The discs were washed thoroughly with diethyl ether and air dried.

Several of the discs prepared above were treated with DMF at 80-100° C. for several hours before washing thoroughly with diethyl ether and air drying.

Example 5

Preparation of Polystyrene-Divinylbenzene 1,4-Divinylbenzene (DVB) (1.63 cm$^3$, 15 mmol), styrene (0.92 cm$^3$, 5.4 mmol), toluene (1.9 cm$^3$) and 1,1-azobis(cyclohexane-carbonitrile) (15 mg) were added to Q-Cel 300 (~80 μm hollow glass spheres) (300 mg). The mixture was cast into discs in a Teflon moulds and the polymerisation was left to go to completion overnight at 100° C. for 2.5 h. The discs were washed thoroughly with dichloromethane and air dried.

An SEM of the product is shown in FIG. 4.

Example 6

Preparation of Silica

Tetramethoxyorthosilane (TMOS) (2.5 cm$^3$) and 3-aminopropyl-trimethoxysilane (APTS) (0.025 cm$^3$) was added to ethanol-water (5 cm³, 95:5 v/v) and mixed thoroughly. This mixture was added to Expancel 920 DEX 80 d30 (200 mg, 13 cm³) and mixed thoroughly. The mixture was cast into discs in a Teflon moulds and the polymerisation was left at 50° C. for several hours. The discs were treated with DMF over ~60 h and washed thoroughly with water before freeze drying.

SEM's of the product is shown in FIGS. 5 and 6.

Example 7

Preparation of Silica containing Hollow Glass Spheres

TMOS (2.5 cm³) and APTS (0.025 cm³) was added to ethanol-water (2.5 cm³, 95:5 v/v) and mixed thoroughly. This mixture was added to Q-Cel 7014 (~100 µm hollow glass spheres) and mixed thoroughly. The mixture was cast into discs in a Teflon moulds and the polymerisation was left at 50° C. for 48 h. The discs were washed thoroughly with water before freeze drying.

An SEM of the product is shown in FIG. 7.

Example 8

Polyacrylamide Containing Hollow Polyacrylonitrile Spheres Encapsulated within Glass Seed Beads Methylene-bis-acrylamide (MBA) (240 mg, 1.55 mmol) was dissolved with warming in N,N-dimethylformamide (DMF) (2.5 cm³). This solution was cooled to room temperature and 2-(dimethylamino)ethylmethacrylate (DMAEM) (0.43 cm³, 0.55 mmol), acrylamide (1.9 g, 26.8 mmol), tetramethylendiamine (TEMEDA) (0.006 cm³, 0.05 mmol) and water added. The mixture was agitated in a round bottom flask until all components dissolved. Expancel 920 DEX 80 d30 (80 µm polyacrylonitrile balloons) (150 mg, 10 cm³) was added and mixed thoroughly before ammonium persulfate solution (0.285 cm³ of 1% w/v) was added to initiate polymerisation. 1 mm diameter glass seed beads (30 cm³) were added to the mixture and the flask momentarily evacuated to draw the polymerisation mixture into the seed beads. The polymerisation was left to go to completion overnight at room temperature.

The seed beads were washed thoroughly with water and any polymer on the surface of the beads removed by abrasion. The water wet beads were freeze dried.

An SEM of the product is shown in FIG. 8.

Example 9

Sections of the discs prepared in Example 2 were used to culture human embryonic stem cells. A population of cells was applied to the disc and fed with conventional nutrients. The stem cells multiplied and spread throughout the 3D structure such that stem cells were produced within the pores of the 3D structure.

The invention claimed is:

1. A 3-dimensional porous polymeric structure comprising a porous polymer structure, wherein the pores are formed by moulding the polymer structure around an array of particles, the particles optionally remaining within the pores of the polymer, and wherein the porous polymeric structure has a pore size range from between 10 to 1000% of the average pore size, wherein the porous polymer is selected from the group consisting of polyacrylamide, polyacrylic acid, polystyrene-divinylbenzene, silica, polystyrene, polydimethylacrylamide, polymethylmethacrylate, polyacrylate, polyurea, polyacryloylmorpholine, plyvinylalcohol, polybetahydroxy ester and polyacrylonitrile, polyalkylene glycol and polyHIPE.

2. A 3-dimensional porous polymeric structure of claim 1 wherein the pore size range is from 75 to 125% of the average pore size diameter.

3. A 3-dimensional porous polymeric structure of claim 1 comprising particles within the pores of the structure.

4. A 3-dimensional porous polymeric structure of claim 3 wherein the particles is are selected from at least one of a cell and a material selected from glass, ceramic, polymer, natural product and metal.

5. A 3-dimensional porous polymeric structure of claim 3 wherein the particles is are hollow.

6. A 3-dimensional porous polymeric structure of claim 3 wherein the particles are spherical or ellipsoidal.

7. A 3-dimensional porous polymeric structure of claim 3 wherein the particles are hollow glass spheres, hollow polymer spheres, yeast cells or wax spheres.

8. A 3-dimensional porous polymeric structure of claim 3 wherein the particles comprise a hollow polymer and have active sites for reaction with a derivative for linking to the porous polymer.

9. A 3-dimensional porous polymeric structure of claim 1 further comprising a functional material supported by the polymer selected from a catalyst, a pharmaceutical active, an agrochemical active, or a biological macromolecule.

10. A process for producing a 3-dimensional porous structure comprising closely packing particles in a zone to provide a 3 dimensional array of the particles, contacting a polymerisable monomer or a solution of a monomer with the array such that the monomer or the solution fills interstitial spaces between the particles and effecting polymerisation of the monomer whereby a polymer structure is formed by moulding around the particles and optionally removing the particles from the structure, wherein the porous polymeric structure has a pore size range from between 1/10 to 10 times the average pore size.

11. The process of claim 10 comprising the step of forming a slurry of the particles in a liquid comprising the monomer and polymerising the monomer.

12. A 3-dimensional porous polymeric structure of claim 1 further comprising a functional material supported by the polymer selected from an initiator species for peptide synthesis, an initiator species for oligonucleotide synthesis, an initiator species for solid phase organic synthesis, a protein and a whole cell.

13. A 3-dimensional porous polymeric structure of claim 1 further comprising a functional material supported by the polymer, wherein the functional material is an enzyme.

* * * * *